(12) United States Patent
Ahluwalia et al.

(10) Patent No.: US 10,398,423 B2
(45) Date of Patent: *Sep. 3, 2019

(54) ORGAN RETRACTOR

(71) Applicants: Prabhat Kumar Ahluwalia, Little Falls, NY (US); Puja Ahluwalia, Little Falls, NY (US)

(72) Inventors: Prabhat Kumar Ahluwalia, Little Falls, NY (US); Puja Ahluwalia, Little Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/709,615

(22) Filed: Sep. 20, 2017

(65) Prior Publication Data

US 2018/0008254 A1 Jan. 11, 2018

Related U.S. Application Data

(63) Continuation of application No. 15/079,141, filed on Mar. 24, 2016, now Pat. No. 9,795,369, which is a continuation of application No. 13/432,960, filed on Mar. 28, 2012, now Pat. No. 9,326,760.

(60) Provisional application No. 61/468,272, filed on Mar. 28, 2011.

(51) Int. Cl.
*A61B 17/02* (2006.01)
*A61B 17/04* (2006.01)
*A61B 17/00* (2006.01)

(52) U.S. Cl.
CPC .......... *A61B 17/0218* (2013.01); *A61B 17/04* (2013.01); *A61B 2017/00557* (2013.01); *A61B 2017/00862* (2013.01); *A61B 2017/0225* (2013.01)

(58) Field of Classification Search
CPC .. A61B 2017/00557; A61B 2017/0225; A61B 2017/22054; A61F 5/003–0073
See application file for complete search history.

(56) References Cited

U.S. PATENT DOCUMENTS

| | | | | |
|---|---|---|---|---|
| 4,246,893 | A * | 1/1981 | Berson | A61F 5/0073 128/898 |
| 2004/0002726 | A1 * | 1/2004 | Nunez | A61B 17/02 606/192 |
| 2007/0149994 | A1 * | 6/2007 | Sosnowski | A61F 5/003 606/192 |
| 2007/0179556 | A1 * | 8/2007 | Ben Haim | A61B 5/053 607/40 |

(Continued)

*Primary Examiner* — Thaddeus B Cox
(74) *Attorney, Agent, or Firm* — Pierson IP, PLLC

(57) ABSTRACT

A medical device of the present invention includes one or more anchors and an elongated member. Advantageously, the elongated member may be coupled to the anchors. The elongated member and anchors are configured to generate a force on a mesentery. The force is sufficient to retract a bowel of the patient into an upper portion of an abdominal cavity of the patient. When the patient is in a slightly angled position, the weight of the medical device pulls the mesentery into the upper abdomen. Since the bowel is connected to the mesentery, the device also indirectly pulls up the bowel. In some implementations of the device, a slight angle may be unnecessary. In others, the device may also inversely retract the mesentery and attached organs into the lower abdomen to facilitate surgical access to the upper abdomen. In some implementations of the device, a slight angle may be unnecessary.

13 Claims, 8 Drawing Sheets

(56) References Cited

U.S. PATENT DOCUMENTS

2011/0100376 A1\* 5/2011 Rousseau ................ A61F 5/566
                                                                                                128/848

\* cited by examiner

ORGAN RETRACTOR

RELATED APPLICATIONS

This application claims the benefit of U.S. Provisional Application No. 61/468,272 filed on Mar. 28, 2011 and entitled "BOWEL RETRACTOR" and incorporated herein in its entirety by reference.

BACKGROUND

Surgeons who operate in the lower abdomen or pelvic area face a number of challenges. In open surgery, or a laparotomy, surgeons sometimes must make a large incision in the belly of the patient to access the bowel and safely displace or shield it out of the surgical area and into the upper abdomen. The large incision is traumatic and increases blood loss, recovery time, and the risk of complications.

In addition, to operate in the lower abdomen or pelvic area surgeons must employ the steep trendelenburg position, which presents a number of problems and risks for healthy patients and enhanced risks for the obese, geriatrics, diabetics, and patients with cardiovascular or respiratory problems. In the trendelenburg position, a patient lies at an incline so that their feet are elevated at an angle above their head, typically 10 to 30 degrees, sometimes 45 degrees. Some common position ranges, for example, include 10 to 15 degrees for open surgery, 10 to 20 degrees for laparoscopic surgery, and 15 to 45 degrees for robotic surgery.

At such inclines, gravity exerts a downward force upon the bowel, such that the bowel falls toward the upper abdomen, thereby leaving a space in the pelvic cavity or lower abdomen 34. FIGS. 5 and 6 show a cross-section of the patient and the effect of transitioning from a flat reclined position (FIG. 5) to a steep trendelenburg position (FIG. 6). Patients typically remain in this position for the duration of the surgery, which may be several hours.

The steeper trendelenburg positions (or angles) may present problems and risks for otherwise healthy patients and enhanced risks for the obese, geriatrics, diabetics, and patients with cardiovascular or respiratory problems. The patient may experience respiratory and cardiovascular challenges, facial edema, intraocular pressure, or stagnation of the blood in the head because of the gravitational force exerted upon the bodily organs which are in reversed orientation. The patient may, in the worst instances, even experience a pulmonary edema, aneurysm, or increased risk of stroke. The trendelenburg position also may concentrate anesthesia in the head by increased blood flow and stasis, which increases risks from anesthesia.

The steep trendelenburg position also strains the lower extremities, which are tied down by stirrups to prevent the patient from sliding off the inclined operating table. For the obese, there is a greater risk of blood stasis in the legs and the feet in addition to compression or injury to the peroneal nerve resulting in foot drop or paralysis.

The steep trendelenburg position also compromises surgical safety. Patients can experience cephalic sliding (i.e., sliding down the operating table head first) during a surgical procedure. Cephalic sliding compromises the surgeon's ability to perform surgery with precision and accuracy, and this heightens the risk of accidental injury to internal organs.

Finally, the steep trendelenburg position may not be steep enough to keep the bowel in the upper abdomen. Sometimes, the bowel may slide to the lower abdomen or pelvic area during surgery. This often happens when patient's anesthesia begins to wear off and the patient begins to breathe, which is not an uncommon occurrence. The inhalations counteract the force of gravity, and sometimes the inhalations push the bowel from the upper abdomen back into the pelvic area or lower abdomen. Sliding of the bowel increases the risk of surgical error or injury, particularly when the surgeon is using sharp surgical tools, cauterizers, and lasers.

Improvements to accessibility of the abdominal and pelvic area during surgery without compromising patient safety are therefore desirable.

SUMMARY

Implementations of the present disclosure overcome the problems of the prior art by providing a medical device. For example, the medical device may include an organ retractor for facilitating positioning of a mesentery or organs connected to a mesentery within an abdominal cavity of a patient. The organ retractor may include a harness. The harness may have an elongated body with a diameter configured for passage through a port or incision. The elongated body may be configured to form into at least one of a U or V or Y or O shape so that a concave side of the shape can extend around and against the mesentery. The harness may also be configured to generate a force on the mesentery to retract the organ of the patient into a portion of the abdominal cavity.

The medical device may also include at least one anchor and an elongated member. The elongated member is coupled to the anchor. The elongated member and anchor are configured to generate a force on the mesentery sufficient to retract the bowel of the patient into a portion of the abdominal cavity.

These and other features and advantages of the implementations of the present disclosure will become more readily apparent to those skilled in the art upon consideration of the following detailed description and accompanying drawings, which describe both the preferred and alternative implementations of the present disclosure.

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

Figure 1:
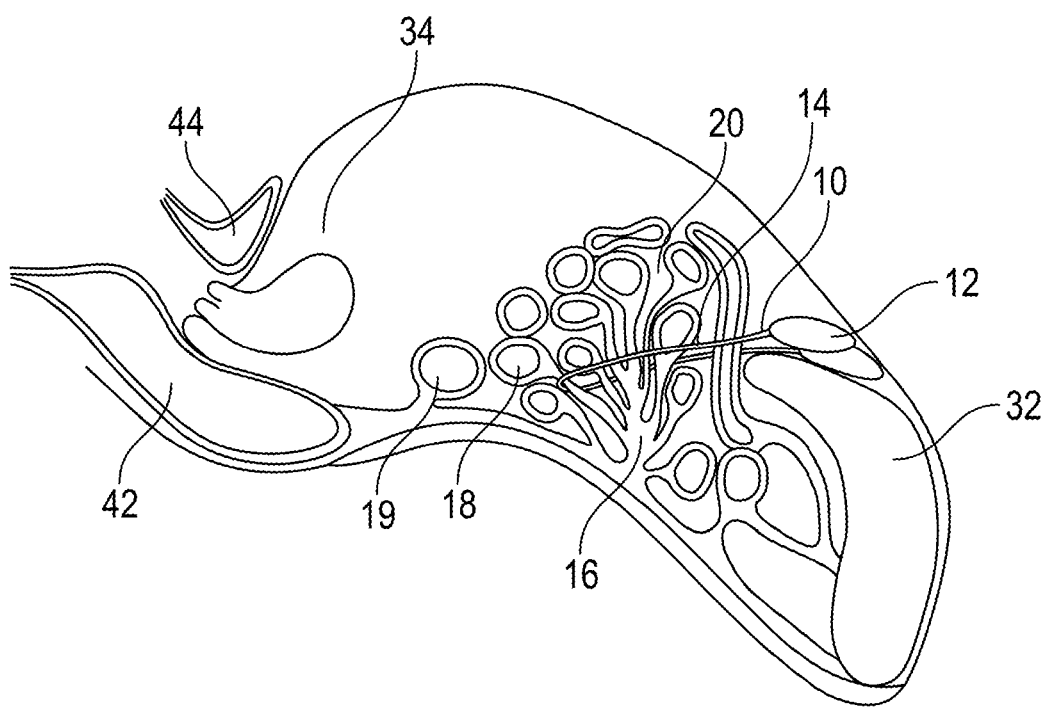
FIG. 1 is a sectional lateral view of a medical device retracting a mesentery 16 and bowel of a patient at the trendelenburg position of 20 degrees or less.
Figure 2:
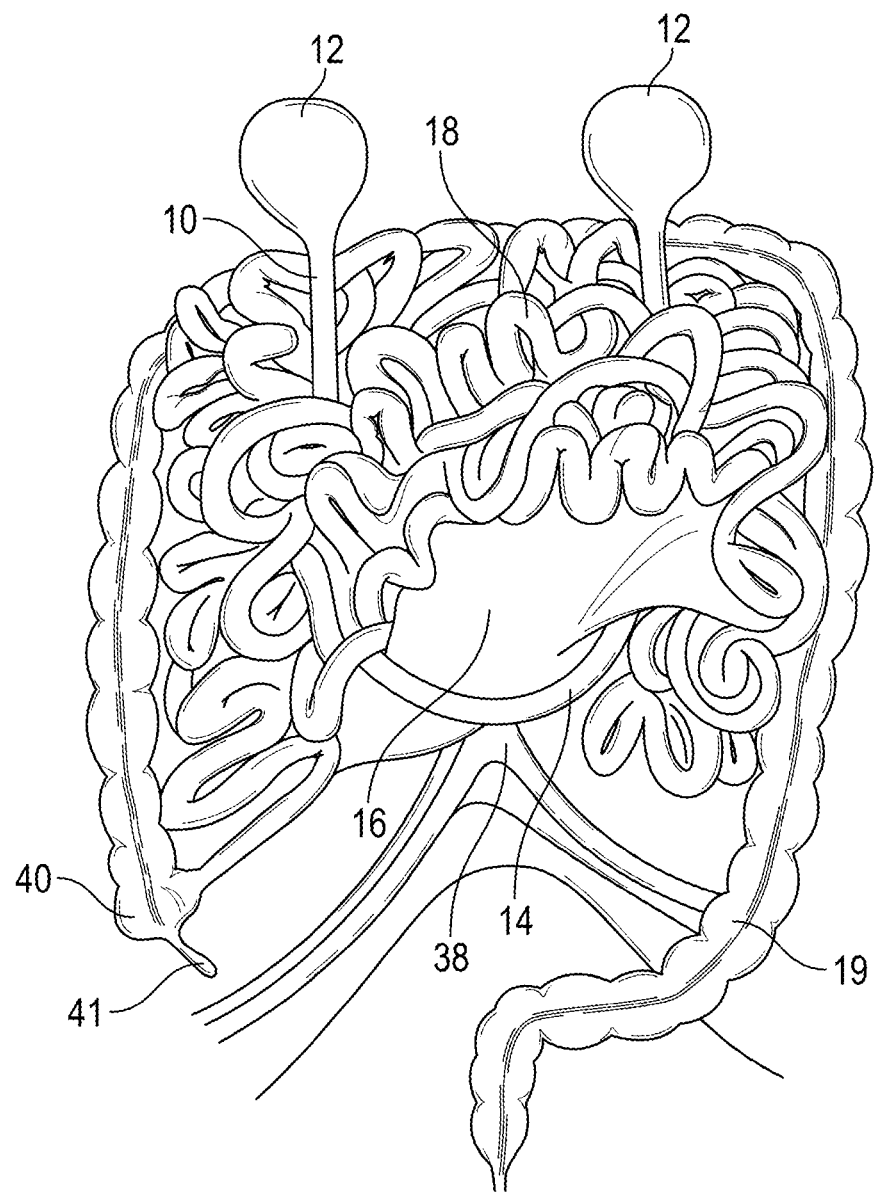
FIG. 2 is an anterior view of the medical device of FIG. 1.
Figure 3:
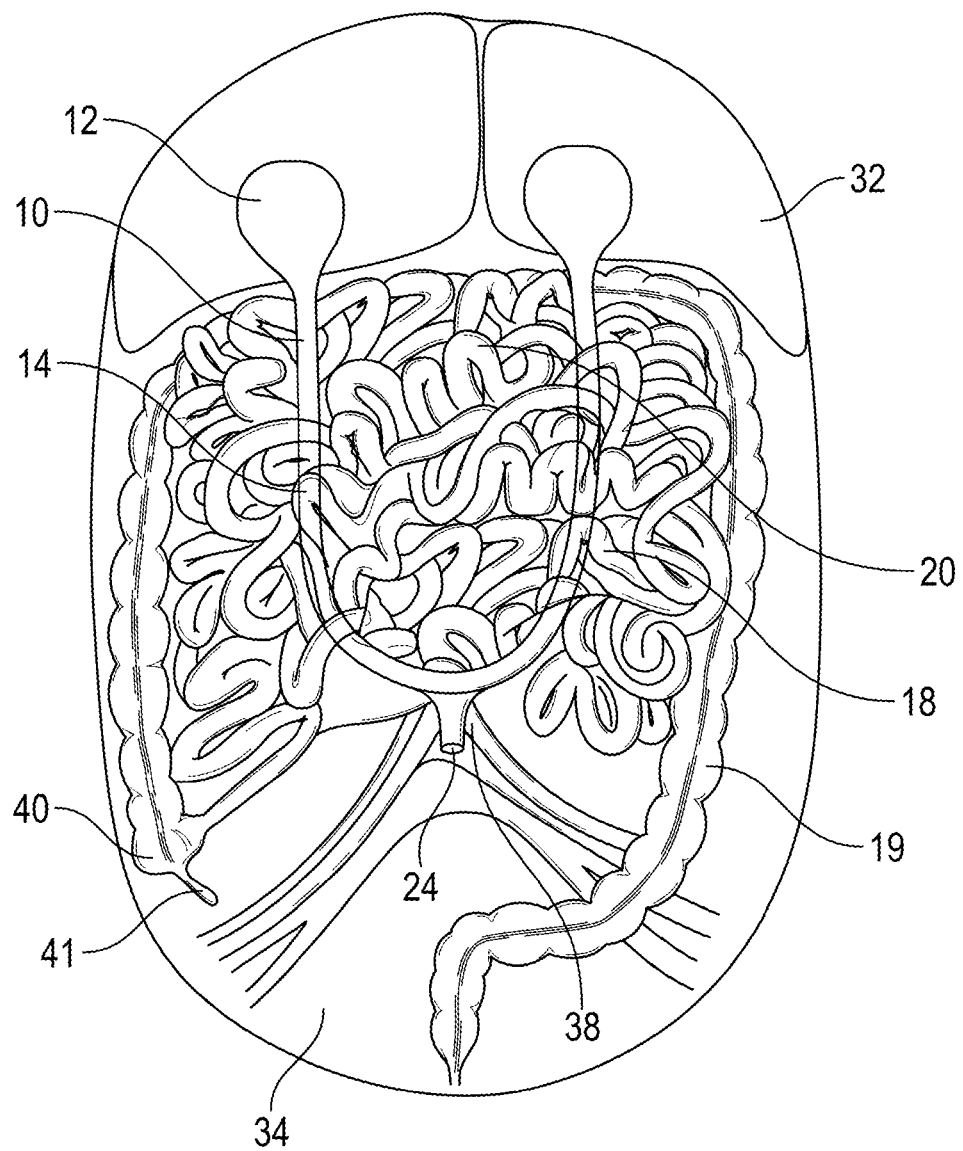
FIG. 3 is another anterior view of the medical device of FIG. 1 resting on the liver 32.

As shown in FIGS. 1-3, a medical device 10 of the present invention includes one or more anchors 12 and an elongated member 14. For example, the ends of the elongated member 14 may be coupled to the anchors 12. The elongated member 14 and anchors 12 are configured to generate a force on a mesentery 16. The force is sufficient to retract a small bowel 18 and portion of a large bowel 19 (both together hereinafter "bowel") of the patient into the upper abdomen 20 of the patient. When the patient is in a slight trendelenburg position, the weight of the medical device 10 due to gravity pulls the mesentery 16 into the upper abdomen 20. Since the bowel is connected to the mesentery 16, the device also indirectly pulls up the connected bowel. In some implementations of the device 10, a slight angle may be unnecessary.

The term "patient" as used herein includes animals as well as humans. For example, the medical device 10 may be employed in veterinary practices.

Figure 4:
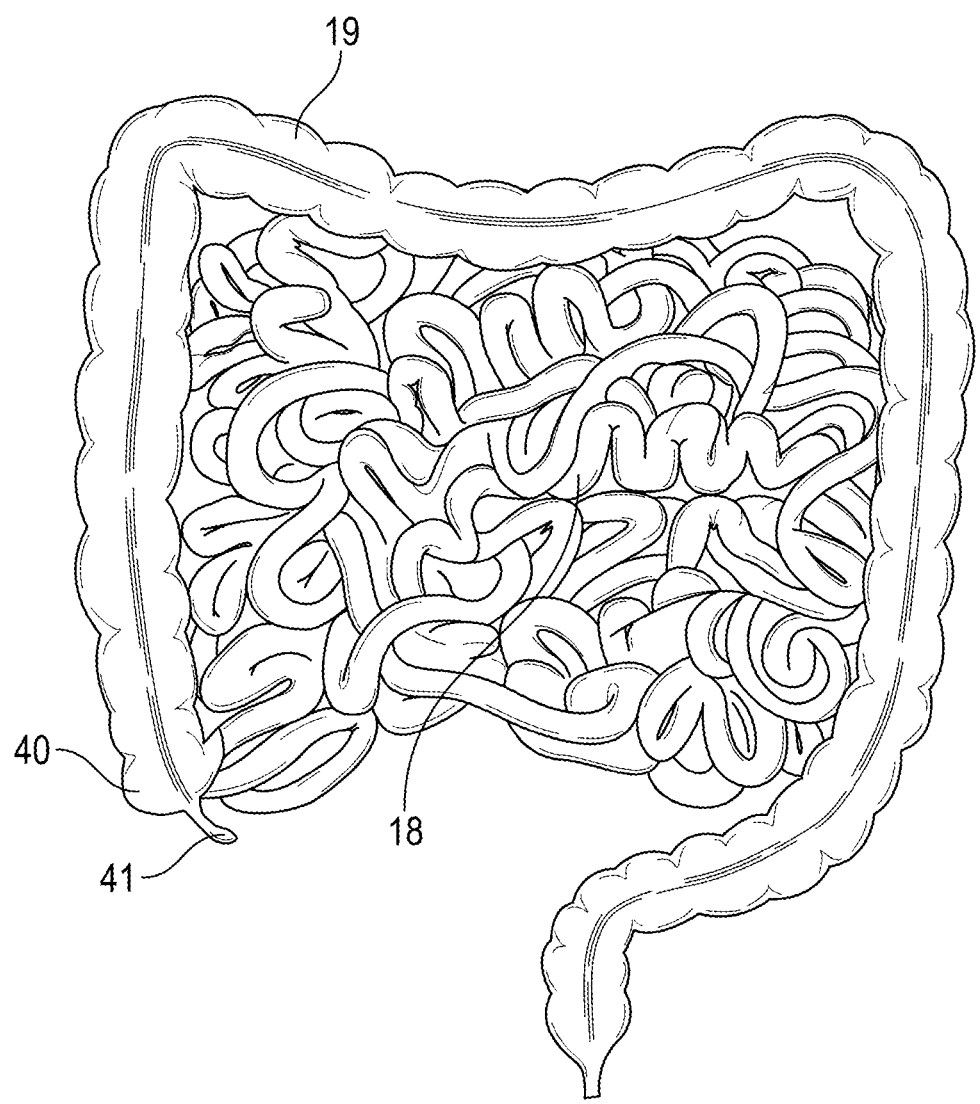
FIG. 4 is an anterior view of a bowel and other anatomy of a supine patient without incline.
Figure 5:
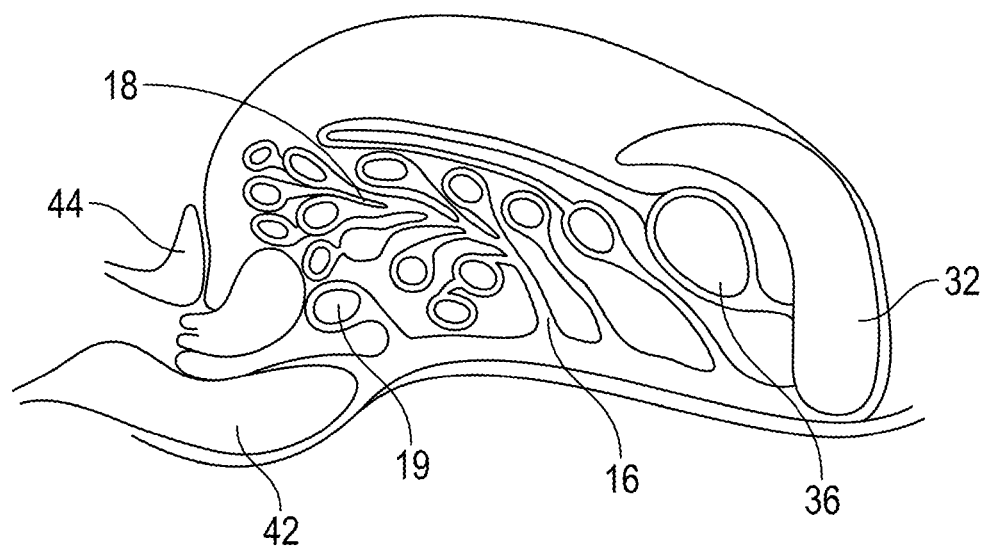
FIG. 5 is a sectional lateral view showing bowel and other anatomy in a supine patient without incline.
Figure 6:
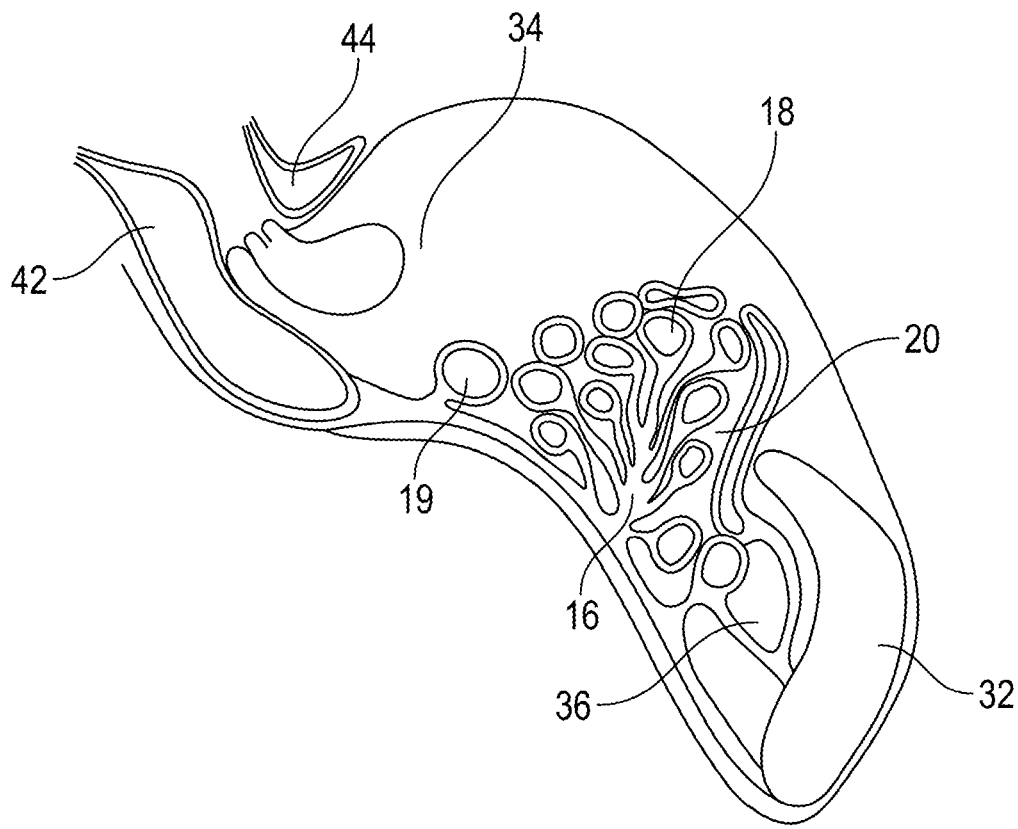
FIG. 6 is a sectional lateral view showing a bowel and other anatomy in a patient in a steep (45 degree) trendelenburg position.
Figure 7:
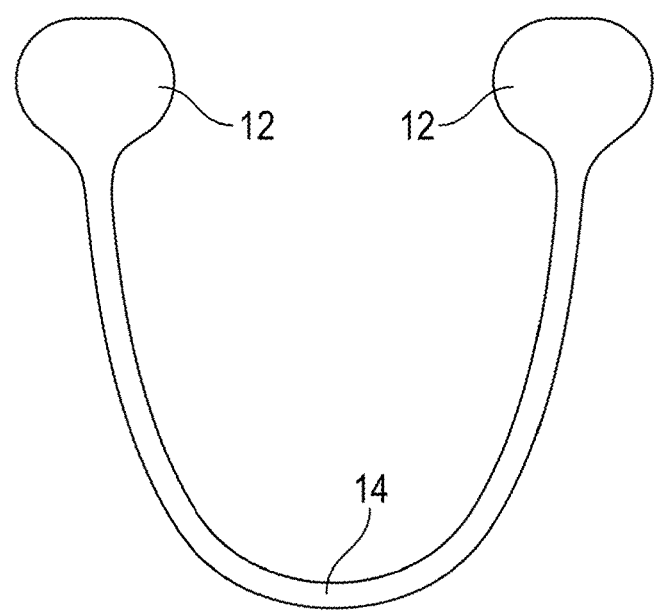
FIG. 7 illustrates an example of a medical device 10 with an elongated member 14 and anchors 12.

The inventor has observed that in a supine position, the bowel fills up the entire abdominal cavity of the patient, as shown in FIG. 4. When viewed in this manner, the bowel is hard to move or manipulate as one mass. However, as shown in FIG. 2, the inventor has also observed that the mesentery 16 of the patient provides an additional attachment that aggregates the mass of the bowel. A mesentery 16 is usually a fold of tissue that attaches the bowel to a body wall. The mesentery 16 anchors the small intestine to the patient's posterior abdominal wall or back wall. Blood vessels, nerves, and lymphatics branch through the mesentery 16 to supply the intestine. The mesentery 16 also supports the sigmoid colon, appendix, transverse colon, and the ascending and descending colon (hereinafter "other organs").

Referring to FIGS. 1-3 and FIG. 7, the elongated member 14 may be constructed of a relatively flexible material and length of small diameter, biocompatible material such as an elastomeric (e.g., rubber or polymeric) tube. The elongated member 14, when used to retract the bowel, may be about 15 cm to 50 cm to fit a range of patient sizes and ages. The elongated member 14 may be supplied in the operating room as a selection of sizes. For example, 15 cm, 30 cm and 50 cm may be provided for selection on site by the surgeon.

Figure 8:
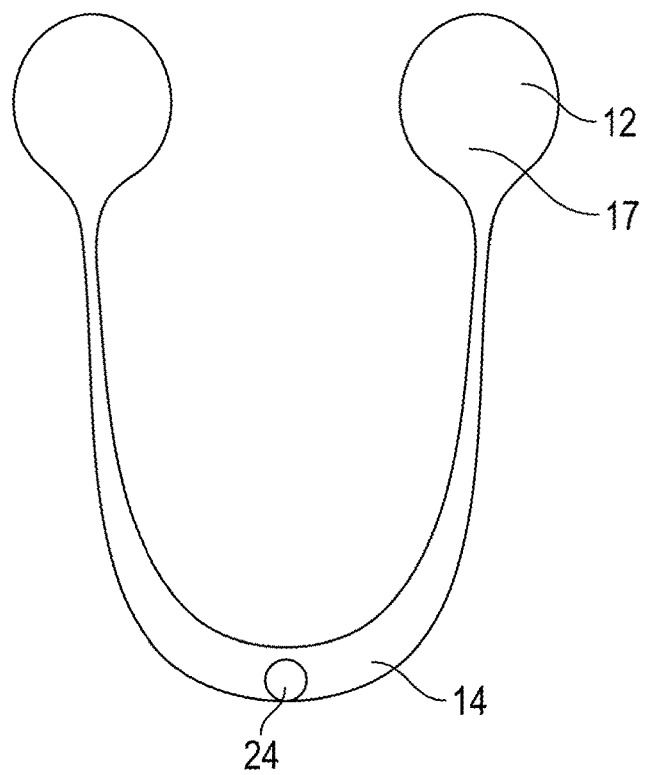
FIG. 8 illustrates another example of a medical device 10 with distensible balloons 17 serving as anchors 12, and an intake valve 24.
Figure 9:
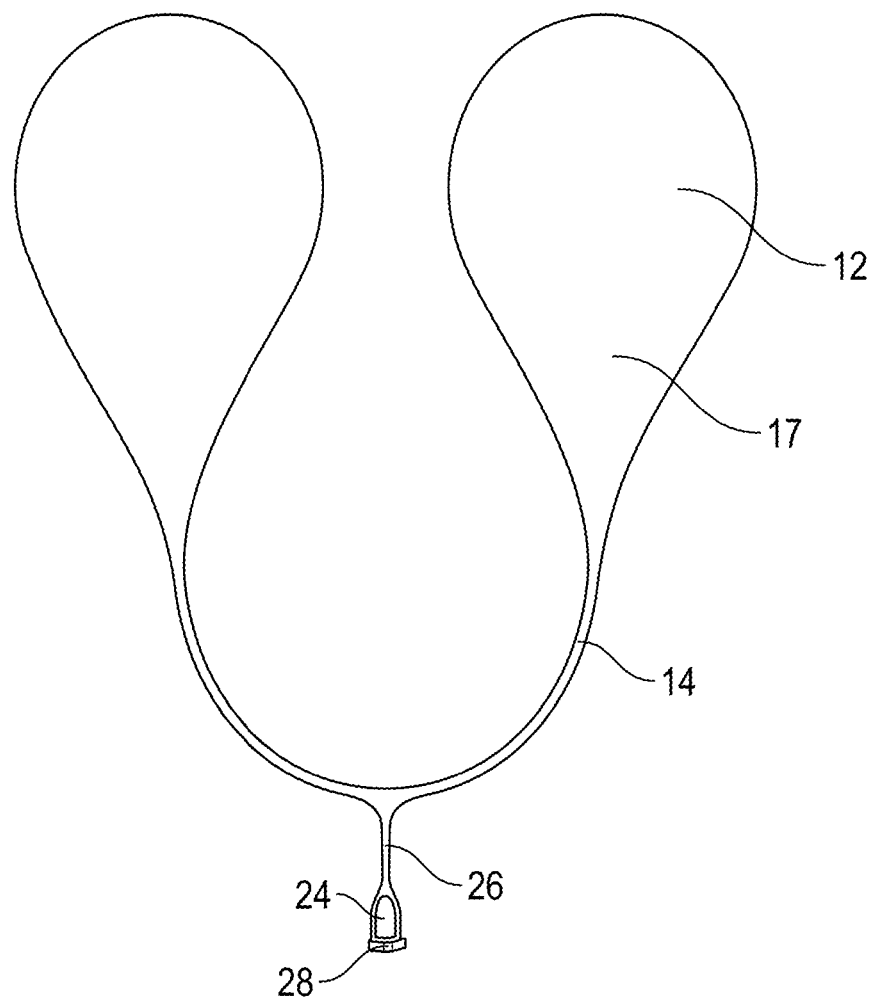
FIG. 9 illustrates another example of a medical device 10 with distensible balloons 17 serving as anchors 12, an intake valve 24, a conduit 26, and a luer lock 28.
Figure 10:
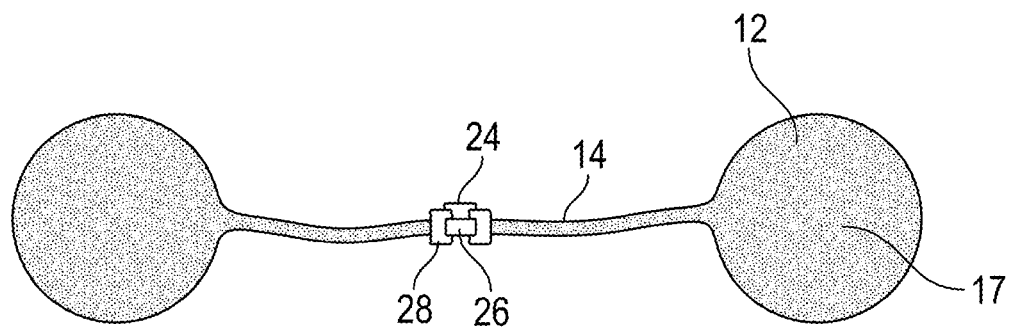
FIG. 10 is a plan view of the medical device of FIG. 9.

Referring to FIG. 8, the elongated member 14 may include an intake valve, port, or opening 24 that is configured to establish fluid communication with a lumen of the elongated member 14. For example, the intake valve 24 may be combined with a luer lock 28, as shown in FIG. 9. The intake valve 24 is configured to receive the tip of a fluid dispenser, such as a syringe. The luer lock 28 is configured to lock the fluid injected by the syringe within the lumen of the elongated member 14. The intake valve 24 may be positioned at a middle portion of or position on the elongated member 14. Referring the FIG. 9, the intake valve 24 may also connect to a conduit 26 that is configured to establish fluid communication with a lumen of the elongated member 14. The connection between the conduit 26 and elongated member 24 may create a Y-shape.

Figure 11:
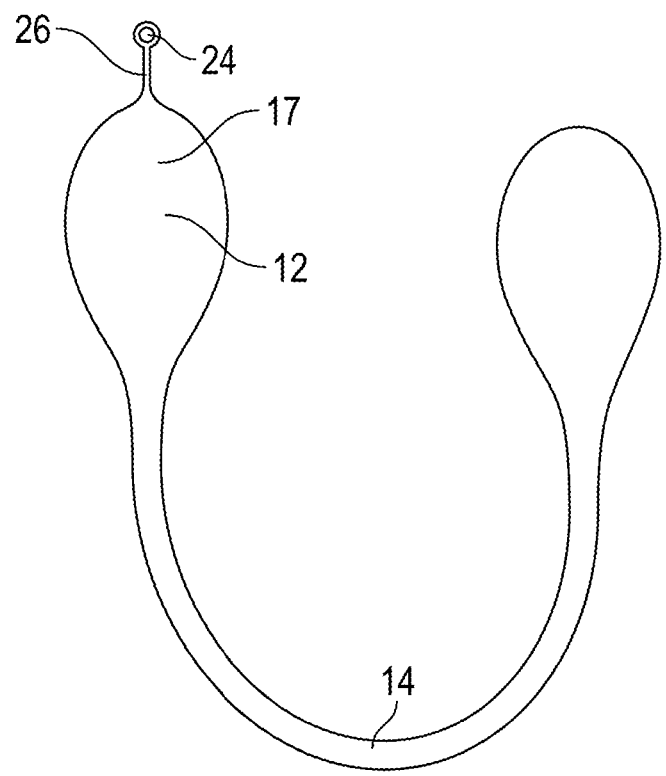
FIG. 11 illustrates an example of a medical device 10 with an intake valve 24 located at the distensible balloon 17.

The intake valve 24 may be, for example, a duck-bill or tuohy borst valve that allows insertion but closes or tightens against fluid loss. If such characteristics are robust, they may negate the need for the luer lock 28, as in FIG. 8. The intake valve 24 may be 3 mm to 8 mm in diameter and may be positioned at preselected points along the elongated member 14. In the illustrated embodiment in FIG. 8 and FIG. 9, the intake valve 24 has a central positioning in anticipation of forming a symmetrical medical device 10 for symmetrical application of force to the mesentery 16 and bowel. Referring to FIG. 11, alternatively the intake valve 24 may be located along any portion of the elongated member 14 or anchors 12.

The fluid within medical device 10 may be a biocompatible fluid that meets regulatory requirements. For example, it may be water or physiologic saline, dextran, malithol or other more dense fluids than saline. Biocompatible fluids guard against adverse effects during a leak. The fluid may also be varied to have different flow rates and densities to control balloon weight, rate, position and distribution of inflation. Also, fluid variations may be employed to change or adapt the amount of weight to change the retraction force of the medical device 10. As will be described below, the fluid may also inflate one or more of the anchors 12.

The elongated member 14 may have a relatively distensible wall so as to allow thickening and inflation by the injection of the fluid. For example, the elongated member 14 may be constructed similar to (but larger in scale than) some angioplasty balloons or balloons used in Foley's catheter, Humi, or V-CARE instruments to stretch or unfold into desired shapes that optimize weight and positioning for retraction of the mesentery 16 and attached bowel.

The distensibility of the wall of the elongated member 14 may be varied through varying thickness, density or material composition to allocate fluid weight more proximally or distally. For example, the wall thickness or density of the elongated member 14 may decrease near its ends (e.g., using a lower density approved by the Food and Drug Administration). The lower density at the ends would increase the elasticity of the ends and promote fluid accumulation at the ends for greater weight and retraction capabilities. In this manner, the ends of the elongated member 14 may become bulbous or balloon anchors 12 integrally formed with remaining portion of the elongated member 14. For example, the distal ends of the elongated member 14 may dilate enough to hold 1 to 10 ounces of fluid. For children, 30 ml of water may be enough. Larger weights may be better for larger, adult patients. Held at an angle, the elongated member 14 injected with fluid resembles a horseshoe. It may also resemble a V or Y.

The anchors 12 may include weights that may be flat, folded, rounded or oval shaped depending upon the expected positioning and amount of weight desired for the medical device 10. The weights may be solid or in the form of pre-shaped distensible balloons 17 at the ends of the elongated member 14. The preformed balloons may hold, for example, 1 to 10 ounces of fluid. Like an area of lower wall density, the balloon shape allows more fluid to accumulate at the distal ends of the elongated member 14.

Although surgical implementations of the medical device 10 may vary, the fluid inflatable elongated member 14 and anchors 12 are well suited for use through small incisions. For example, the surgeon (or other healthcare personnel) may form an incision in the pelvis or the patient's abdomen. In laparoscopic and robotic surgeries, the incision may accommodate a port. The term "port" as used herein refers to any at least partially restricted opening in a patient either formed through surgery, existing due to natural anatomy, or created with or facilitated by a medical device that allows insertion and positioning of medical tools through an incision to perform surgical procedures or scoped access. For example, an incision in the belly button or naval may accommodate a port with a port diameter of 5 to 15 mm or more for laparoscopic surgeries or 8 to 12 mm or more for robotic surgeries. Alternatively, in mini-lapartomies, the surgeon may make an incision without a port to insert the medical device 10.

After incision, the surgeon slides the elongated member 14 (including both free ends) except, the luer lock 28 into the incision hole. The luer lock is retained outside the patient, while the elastomeric elongated member 14 is inside the patient's belly.

After insertion, the syringe is attached to the intake valve 24 and fluid is injected therethrough into the lumen of the elongated member 14. After the fluid is injected, the luer lock 28 automatically closes. The locked medical device 10 is dropped into the belly.

In laparoscopic and robotic surgeries, the surgeon may then place the surgical port onto the incision hole (that holds open the surgical opening) and then insert the laparoscope or other instrument. Alternatively, the surgeon may place the surgical port immediately onto the incision hole after incision and then slide the elongated member 14 through a port hole, and retain the luer lock outside patient and port hole for fluid injection.

After insertion of the medical device 10 into the patient, the surgeon places the patient into a trendelenburg position until gravity retracts the bowel to the desired location in the upper abdomen 20, such as shown by FIG. 1. The surgeon grasps the middle portion of the elongated member 14 near the luer lock 28 with a surgical tool. The middle portion of the elongated member 14 is placed onto the mesentery 16. Gravity forces the anchors 12 or ends of the elongated member to the upper quadrants of the abdomen. The anchors 12 are then placed either on top of the right and left lobes of the liver 32, between the liver 32 and the anterior abdominal wall, or alternatively, below the liver bed, for example in Morrison's Pouch or the Lesser Sac. The surgeon may also place the anchor in the space between the liver 32 and the posterior abdominal wall (back wall) or stomach 36.

The surgeon then reduces the trendelenburg angle (removing the caudal or cephalic decline) until the device is on the verge of no longer retracting the mesentery 16 and attached bowel at the desired location. If the angle is reduced too much, the angle can be increased when the medical device 10 is no longer retracting the mesentery. The angle will vary depending upon the size of the patient, body mass index and variations in anatomy (location and size of the relevant organs). Generally, thin patients may have lower angles, and heavy patients may need steeper angles.

The anchors 12 may hold tension on the elongated member 14 through a combination of gravitational and/or friction forces. The component extending along the elongated member 14 of the gravitational force may be sufficient itself to offset the force exerted by the mesentery. The friction force may be between the organ and the anchors 12.

After the medical device 10 is in place and retracting the mesentery 16 and associated bowel or other organs, the surgeon performs the desired surgery.

After surgery, the medical device 10 may be removed. For example, the surgeon uses a surgical tool to grasp the luer lock 28 and pulls the lock toward and then through the incision hole. To facilitate removal, the medical device 10 may include a string that extends from within the patient's body to outside of the incision or port for the duration of the surgery. The surgeon may pull on the string to bring the medical device 10 to the incision hole or port for removal.

When the medical device 10 is brought to the incision hole for removal, the luer lock 28 is further pulled out of the incision hole until the luer lock is protruding outside of the hole. At this point, the elongated member 14 is still in the abdominal cavity. In laparoscopic or robotic surgeries, the surgeon may simultaneously remove the port placed on top of the incision hole. Various other ports, scopes and instruments may then be removed, if necessary or desired.

The syringe is inserted into the intake valve 26. The elongated member 14 and anchors 12 (if fluid filled) are deflated using the syringe. (In addition, or alternatively, the medical device 10 could be inflated and deflated within the patient's abdomen using an irrigation device). The deflated medical device 10 is then removed from the incision hole entirely. The surgeon stitches or closes the incision hole.

Figure 12:
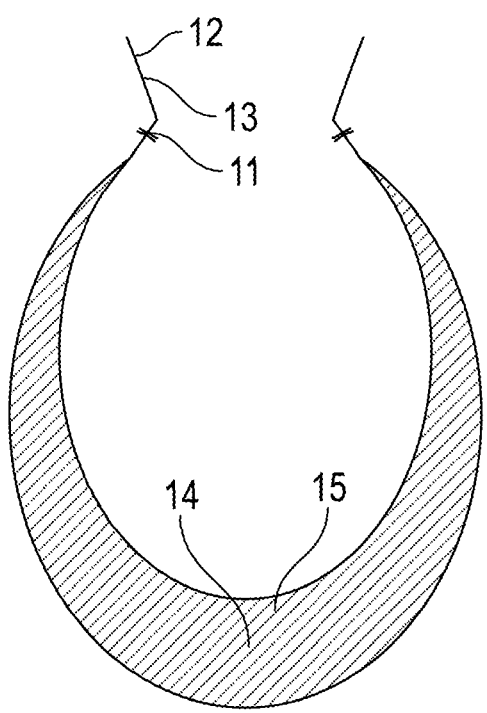
FIG. 12 illustrates another example of a medical device 10 with a strap 15 serving as the elongated member 14 and needles 13 serving as anchors 12.

The medical device 10 may have other implementations. For example, elongated member 14 may have other configurations as long as it has sufficient length to exert a force on the mesentery 16 and bowel (or other organs) sufficient to retract it into the upper abdomen 20. As shown in FIG. 12, the elongated member 14 could include a strap, belt, harness, or mesh 15 which is configured to wrap around a distal end of the mesentery 16. The elongated member 14 may have or be configured into a U-shape, V-shape, or Y-shape with the apex at the distal mesentery 16 or could be doubly wrapped into an O-shape, or some intermediate shapes. These shapes are configured to extend around a portion of the mesentery to provide a consolidated grip to control the otherwise loose bowel or other organs.

The elongated member 14 may be a solid-cross section material, such as a cord or line constructed of polymer or textile. Other materials include plastic, metal, cloth, textiles, synthetic fibers, nylon, or rubber. The strap, belt, harness, mesh 15 or other elongated member 14, which wraps around a part of mesentery 16, may be of the same or different material as the anchors 12. For example, the anchors 14 may include plastic, metal, cloth, synthetic fibers, nylon, rubber, weighted balls, sheathed material, sheathed fluid compatible with the human body or any material FDA approved for use in the body. The anchors 12 may include weights or weighted balloons. The anchors 12 could also include metal masses or clips (or other magnetically sensitive material such as a rubber-iron matrix or iron ball weights) where a corresponding magnet which exerts an attraction magnetic force upon the metal rests on top of the patient's abdomen on the skin to maintain the desired level of retraction.

The anchors 12 could also be of different material than the elongated member 14. For example the anchors 12 may include clips, hooks, or clamps that attach to or pierce through an inner layer of the anterior abdominal wall, such as the frenulum or the peritoneum. The anchors 12 could also include needles 13 that pierce through the anterior abdominal wall to provide appropriate traction. As shown in FIG. 12, the needles 13 could be attached to a thread 11, so that once the needles 13 are pierced entirely through the anterior abdominal wall, the needles may be cut, leaving the threads, which may then be adjusted, tied, taped, or clamped onto the patient's skin or another surface to retain the desired amount of retraction.

As noted above, the elongated member 14 may include or provide some weight to the medical device 10. For example, the elongated member 14 could include a string of weighted balls, sheathed material, a fluid sheath compatible with the human body (e.g., a cylindrical balloon filled with water). FDA materials are generally preferred. The elongated member, when including some significant portion of the weight of the medical device 10, may define one or more receptacles for holding the weighted balls, sheathed material or fluid. The receptacles are defined within the body of the elongated member 14. For example, the elongated member 14 may be a sheath defining an elongated lumen extending between its ends for holding fluid or other weights, such as the weighted balls. In other alternatives, the medical device 10 may be weighted uniformly along the elongated member 14.

The medical device 10 may have other applications, particularly for surgeries on the upper abdomen. In particular, the surgeon may place the elongated member 14 upon the transverse colon and/or omentum and place the anchors 12 in the lower abdomen or pelvic area, thereby retracting the mesentery and attached organs into the lower abdomen or pelvic area and creating visual and spatial access to the upper abdomen. Applying the medical device 10 in this reverse fashion allows surgeons to operate on upper abdominal organs such as the liver, stomach and gall bladder.

The medical device 10 and associated surgical procedures may have many advantages. In open surgeries, the device allows the surgeon to make a smaller incision, thereby avoiding trauma and blood loss. In all surgery modalities (open, laparoscopic, and robotic), the device allows the surgeon to operate in the pelvic cavity or lower abdomen 34 with unobstructed access to the bladder 44, rectum 42, uterus and other pelvic organs without putting the patient in a steep trendelenburg position. For example, the device 10 allows the patient to be inclined at less than 20 degrees, or even as low as 0 degrees. This is especially beneficial in robotic pelvic surgeries where patients often require a steep trendelenburg position.

Advantages of avoiding the steep trendelenburg include reducing strain on the respiratory system when the patient is on ventilation. There is also less impact on the cardiovascular system. Optimal or normal blood flows to the head, reducing facial edema, the risk of undiagnosed aneurysms, and associated anesthesia risks. The lower extremities are less strained, and as a result there is less risk of compression or injury to the peroneal nerve resulting in foot drop or paralysis. Surgery is safer without cephalic sliding of the body. Avoiding the steep trendelenburg also reduces risk factors in patients with diabetes, hypertension or obesity.

The device also offers other advantages. The device provides the surgeon a clear view of the aorta and common iliacs 38 to avoid accidental injury to the major vessel during operations in the pelvic cavity 34 and abdomen. The device also provides clear viewing access to the ureters and accompanying veins. This visual access is particularly important when removing cancerous tissue. When the appendix must be examined (e.g., in cases of appendicitis), the device also retracts the bowel and cecum 40 for easier surgical and visual access to the appendix 41, as shown in FIG. 2 and FIG. 3.

A number of aspects of the systems, devices and methods have been described. Nevertheless, it will be understood that various modifications may be made without departing from the spirit and scope of the disclosure. Accordingly, other aspects are within the scope of the following claims.

10 medical device
11 thread
12 anchor
13 needle
14 elongated member
15 strap
16 mesentery
17 distensible balloon
18 small bowel
19 large bowel
20 upper abdomen
26 conduit
24 intake valve
28 luer lock
32 liver
34 pelvic cavity or lower abdomen
36 stomach
38 aorta and common iliacs
40 cecum
41 appendix
42 rectum
44 bladder

The invention claimed is:

1. A removable device for retracting an organ of a patient, the device including:
   an elongated member comprised of a flexible lumen configured to be temporarily inserted into an opening in an abdominal wall of the patient during a surgical procedure, the elongated member being configured to freely hang within an abdominal cavity of the patient, wherein the elongated member is configured to wrap around, retract, and control a positioning of the organ within an abdominal cavity to create a visual and spatial access within the abdominal cavity during the surgical procedure;
   a first balloon is positioned at a first end of the elongated member; and
   a second balloon is positioned at a second end of the elongated member, wherein the removable device is configured to be removed from the patient after the surgical procedure;
   a freely hanging inlet positioned on the elongated member between the first balloon and the second balloon, the inlet being configured to receive fluid to supply the fluid to both the first balloon and the second balloon, wherein the inlet is configured to freely hang within the abdominal cavity of the patient.

2. The system of claim 1, wherein the elongated member is configured to retract the organ by anchoring the first balloon into a first portion of the abdominal cavity and anchoring the second balloon into a second portion of the abdominal cavity.

3. The system of claim 1, including:
   a conduit configured to connect with the elongated member and extend out of a port or opening.

4. The system of claim 1, wherein the first balloon is configured to hold up to 10 ounces of fluid.

5. The system of claim 1, wherein the first end and the second end of the elongated member are configured to be anchored into a portion of the abdominal cavity.

6. The system of claim 1, wherein the first end and the second end of the elongated member are configured to be anchored into an upper portion of the abdominal cavity.

7. A method for retracting an organ comprising:
temporarily inserting an elongated member comprised of a flexible lumen, a first balloon, and second balloon into an opening in an abdominal wall during a surgical procedure, the first balloon being positioned at a first end of the elongated member, and the second balloon being positioned at a second end of the elongated member;
inflating the first balloon and the second balloon through an inlet positioned on the elongated member between the first balloon and the second balloon;
creating a visual and spatial access within the abdominal cavity during the surgical procedure based on the fluid being inserted into the first balloon and the second balloon;
removing the elongated member, first balloon, and second balloon after the surgical procedure.

8. The method of claim 7, further comprising:
anchoring the first balloon into a first portion of the abdominal cavity;
anchoring the second balloon into a second portion of the abdominal cavity; and
retracting, via the elongated member, the organ.

9. The method of claim 7, further comprising:
creating gravitational tension by increasing a weight of the first balloon and a weight of the second balloon.

10. The method of claim 1, further comprising:
connecting a conduit with the elongated member.

11. The method of claim 7, further comprising:
inflating the first balloon with up to ten ounces of fluid.

12. The method of claim 7, further comprising:
anchoring the first end and the second end of the elongated member into a portion of the abdominal cavity.

13. The method of claim 7, further comprising:
anchoring the first end and the second end of the elongated member into an upper portion of the abdominal cavity.

* * * * *